United States Patent
Scheberle

(10) Patent No.: US 8,192,476 B2
(45) Date of Patent: Jun. 5, 2012

(54) GARMENT FOR THERAPEUTIC COMFORT TO WOMEN EXPERIENCING BREAST DISCOMFORT

(76) Inventor: Angela Scheberle, Evansville, IN (US)

( * ) Notice: Subject to any disclaimer, the term of this patent is extended or adjusted under 35 U.S.C. 154(b) by 1341 days.

(21) Appl. No.: 11/890,048

(22) Filed: Aug. 3, 2007

(65) Prior Publication Data
US 2008/0033517 A1    Feb. 7, 2008

Related U.S. Application Data

(60) Provisional application No. 60/835,234, filed on Aug. 3, 2006.

(51) Int. Cl.
*A61F 7/00* (2006.01)
*A41D 1/02* (2006.01)

(52) U.S. Cl. ............ 607/108; 607/112; 450/38; 2/102

(58) Field of Classification Search .......... 607/108, 607/112; 2/102; 450/38
See application file for complete search history.

(56) References Cited

U.S. PATENT DOCUMENTS

| | | | | |
|---|---|---|---|---|
| 2,403,676 A * | 7/1946 | Modlinski | ............... | 2/94 |
| 2,928,396 A * | 3/1960 | O'Dell | ............... | 450/30 |
| 3,847,139 A * | 11/1974 | Flam | ............... | 600/549 |
| 3,950,789 A * | 4/1976 | Konz et al. | ............... | 2/93 |
| 3,995,621 A * | 12/1976 | Fletcher et al. | ............... | 600/474 |
| 4,580,408 A * | 4/1986 | Stuebner | ............... | 62/259.3 |
| 4,856,294 A * | 8/1989 | Scaringe et al. | ............... | 62/259.3 |
| 5,050,595 A * | 9/1991 | Krafft | ............... | 607/108 |
| 5,063,614 A * | 11/1991 | McSheffery | ............... | 2/94 |
| 5,072,875 A * | 12/1991 | Zacoi | ............... | 607/104 |
| 5,146,625 A * | 9/1992 | Steele et al. | ............... | 2/102 |
| 5,235,974 A * | 8/1993 | Miller | ............... | 607/108 |
| 5,257,956 A * | 11/1993 | Ewen | ............... | 450/1 |
| 5,302,806 A * | 4/1994 | Simmons et al. | ............... | 219/211 |
| 5,305,471 A * | 4/1994 | Steele et al. | ............... | 2/102 |
| 5,415,222 A * | 5/1995 | Colvin et al. | ............... | 165/46 |
| 5,441,534 A * | 8/1995 | MacWinnie et al. | ............... | 607/108 |
| 5,484,448 A * | 1/1996 | Steele et al. | ............... | 607/108 |
| 5,507,794 A * | 4/1996 | Allen | ............... | 607/112 |
| 5,679,052 A * | 10/1997 | Rucki | ............... | 450/57 |
| 5,690,537 A * | 11/1997 | Kalmus | ............... | 450/57 |
| 5,708,978 A * | 1/1998 | Johnsrud | ............... | 2/102 |
| 5,787,505 A * | 8/1998 | Piwko et al. | ............... | 2/115 |

(Continued)

*Primary Examiner* — Roy Gibson
*Assistant Examiner* — Kaitlyn Smith
(74) *Attorney, Agent, or Firm* — Gary K. Price

(57) ABSTRACT

A garment for therapeutic comfort to women experiencing breast discomfort. The garment including an inner side having a first vertical side adjacent a second vertical side. A first layer is attached to the first vertical side and to the second vertical side such that each first layer is disposed over a breast region of the wearer. A first chamber for receiving hot or warm therapy is defined between each first layer and the inner side. A first opening to access the first chamber is defined between first and second ends of the first layer. A side opening in communication with the first chamber can further be disposed between the first layer and the inner side. A second layer is attached to each of the first layers such that each second layer is disposed over the nipple area of the wearer. A second chamber is defined between the first and second layers. A second opening to access the second chamber is defined between first and second ends of the second layer. A lower layer is attached to the inner side such that each lower layer is disposed over the wearer's abdominal area. A lower chamber is defined between the lower layer and inner side. A lower opening to access the lower chamber is defined between first and second ends of the lower layer.

15 Claims, 3 Drawing Sheets

U.S. PATENT DOCUMENTS

| | | | |
|---|---|---|---|
| 6,055,668 A * | 5/2000 | Gros et al. | 2/69 |
| 6,080,037 A * | 6/2000 | Lee et al. | 450/38 |
| 6,198,204 B1 * | 3/2001 | Pottenger | 310/326 |
| 6,241,715 B1 * | 6/2001 | Houser et al. | 604/385.07 |
| 6,394,879 B1 * | 5/2002 | Paige | 450/38 |
| 6,464,717 B1 * | 10/2002 | Smith et al. | 607/108 |
| 6,681,399 B1 * | 1/2004 | Kerr | 2/2.5 |
| 6,927,316 B1 * | 8/2005 | Faries et al. | 602/43 |
| 7,081,034 B1 * | 7/2006 | Zoellner | 450/54 |
| 7,086,925 B2 * | 8/2006 | Kaye et al. | 450/58 |
| 7,309,275 B1 * | 12/2007 | Morales | 450/38 |
| 7,448,936 B1 * | 11/2008 | Kemp-Dorsey | 450/36 |
| 2001/0037076 A1 * | 11/2001 | Shelton | 602/7 |
| 2002/0016984 A1 * | 2/2002 | Poholski | 2/94 |
| 2002/0092312 A1 * | 7/2002 | Head | 62/259.3 |
| 2002/0153126 A1 * | 10/2002 | Clemente | 165/46 |
| 2004/0147989 A1 * | 7/2004 | Terakita et al. | 607/108 |
| 2004/0177425 A1 * | 9/2004 | Kerr | 2/2.5 |
| 2005/0223465 A1 * | 10/2005 | Williams et al. | 2/102 |
| 2005/0223466 A1 * | 10/2005 | Jennings et al. | 2/102 |
| 2006/0036304 A1 * | 2/2006 | Cordani et al. | 607/108 |
| 2006/0129212 A1 * | 6/2006 | Halvorson et al. | 607/96 |
| 2006/0253954 A1 * | 11/2006 | Music | 2/115 |
| 2006/0276089 A1 * | 12/2006 | Amarasinghe et al. | 442/121 |
| 2007/0249264 A1 * | 10/2007 | Rhodes | 450/38 |
| 2007/0299489 A1 * | 12/2007 | Francis et al. | 607/108 |
| 2008/0125842 A1 * | 5/2008 | Petitt | 607/108 |
| 2008/0141696 A1 * | 6/2008 | Fuchs | 62/259.3 |
| 2008/0195065 A1 * | 8/2008 | Renzin et al. | 604/290 |
| 2008/0201818 A1 * | 8/2008 | Nilforushan et al. | 2/69 |
| 2009/0217440 A1 * | 9/2009 | Sutker | 2/114 |
| 2010/0089897 A1 * | 4/2010 | Bart | 219/211 |
| 2011/0041229 A1 * | 2/2011 | Niemi et al. | 2/69 |
| 2011/0083248 A1 * | 4/2011 | Johson | 2/102 |

* cited by examiner

GARMENT FOR THERAPEUTIC COMFORT TO WOMEN EXPERIENCING BREAST DISCOMFORT

CROSS REFERENCES TO RELATED APPLICATIONS

U.S. Provisional Application for Patent No. 60/835,234, filed Aug. 3, 2006, with title "Garment for Therapeutic Comfort to Women Experiencing Breast Discomfort" which is hereby incorporated by reference. Applicant claims priority pursuant to 35 U.S.C. par. 119(e)(i).

STATEMENT AS TO RIGHTS TO INVENTIONS MADE UNDER FEDERALLY SPONSORED RESEARCH AND DEVELOPMENT

Not Applicable

BACKGROUND OF THE INVENTION

1. Field of the Invention

The present invention relates to garments worn by women, and more particularly, to a therapeutic upper garment such as a blouse or shirt having means for receiving heated or cooled breast packs to provide comfort to women experiencing breast discomfort.

2. Brief Description of Prior Art

Many women suffer the discomfort of swelling and/or tenderness of the breast due to various reasons including postpartum breast engorgement and enlargement, breast enlargement or reduction surgery, as well as other type procedures and conditions that result in breast discomfort. Doctors treating women who suffer such conditions often recommend warm or cold therapy often in the form of a breast pack that is intended to be retained in position within the user's bra. However, often the available packs fail to conveniently fit beneath a bra. The prior art discloses bras specially designed for receipt of conventional packs. These bras are generally unflattering to the wearer and consist basically of familiar, expected and obvious structural configurations in the crowded art.

It should be appreciated that there exists a continuing need for a comfortable fitting garment that is stylish yet designed to receive cold therapy or warm therapy to give comfort to the wearer experiencing breast discomfort. The present invention fulfills these needs and provides further related advantages.

SUMMARY OF THE INVENTION

The present invention is a garment for therapeutic comfort to women experiencing breast discomfort. The garment includes an inner side having a first vertical side adjacent a second vertical side. The inner side of each of the first and second vertical sides include a first layer attached to the inner side, and preferably having thermal material disposed between the first layer and the inner side. In application, each first layer is disposed over a breast region of the wearer. The thermal material defines a first chamber disposed between the first layer and inner side for receiving hot or warm therapy such as a breast pack. A first opening to access the first chamber is defined between first and second ends of the first layer. A side opening in communication with the first chamber can be disposed along the second end of the first layer.

A second layer is attached to the first layer, and preferably having thermal material disposed between the layers. The second layer is primarily disposed over the nipple area of the wearer. The thermal material defines a second chamber disposed between the first and second layers for receiving hot or warm therapy such as a breast pack. A second opening to access the second chamber is defined between first and second ends of the second layer.

DESCRIPTION OF THE PREFERRED EMBODIMENT

Figure 1:
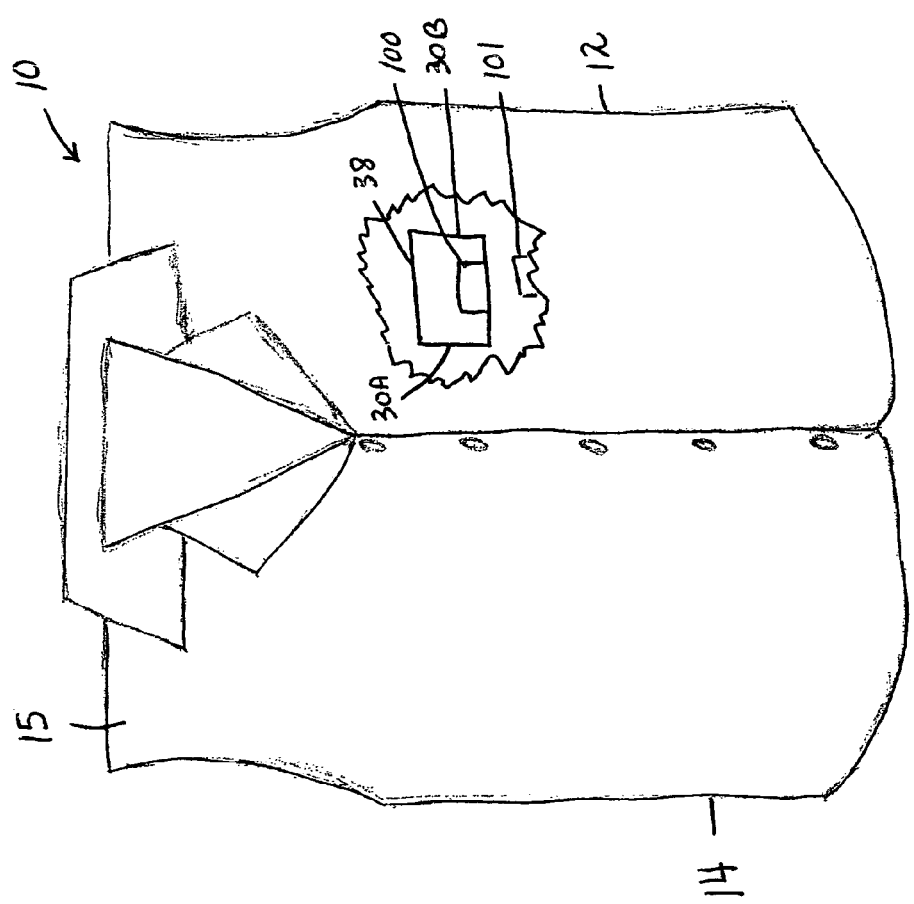
FIG. 1 is a front view of the outer surface of a preferred embodiment of the present invention, a garment for therapeutic comfort to women experiencing breast discomfort.

In accordance with the present invention, a garment for therapeutic comfort to women experiencing breast discomfort is disclosed. The garment is directed to an article of clothing worn by a woman that includes means for receiving cold therapy or warm therapy to provide comfort to the wearer. Specifically, it will be noted in the drawings that the garment of the present invention provides an attractive means for women to comfortably wear breast packs known in the art to relieve discomfort in the breast region. In the broadest context, the garment of the present invention consists of components configured and correlated with respect to each other so as to attain the desired objective.

Figure 2:
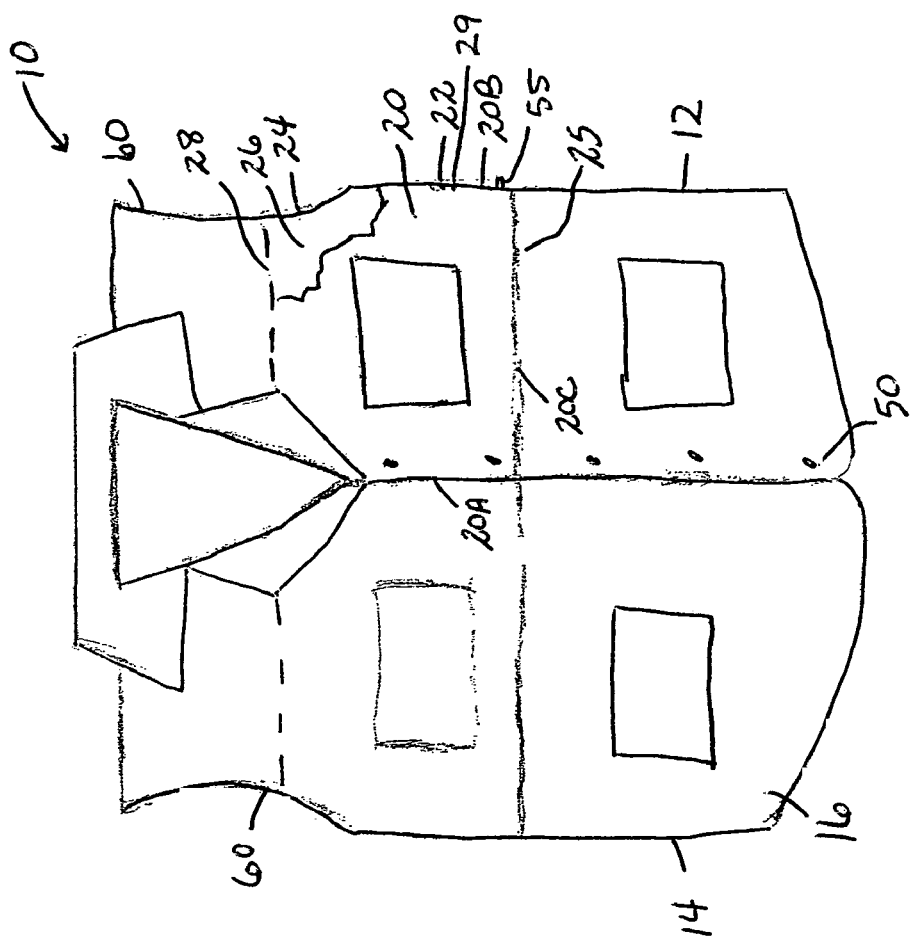
FIGS. 2 and 3 are front views of the inner surface of the garment of FIG. 1
Figure 3:
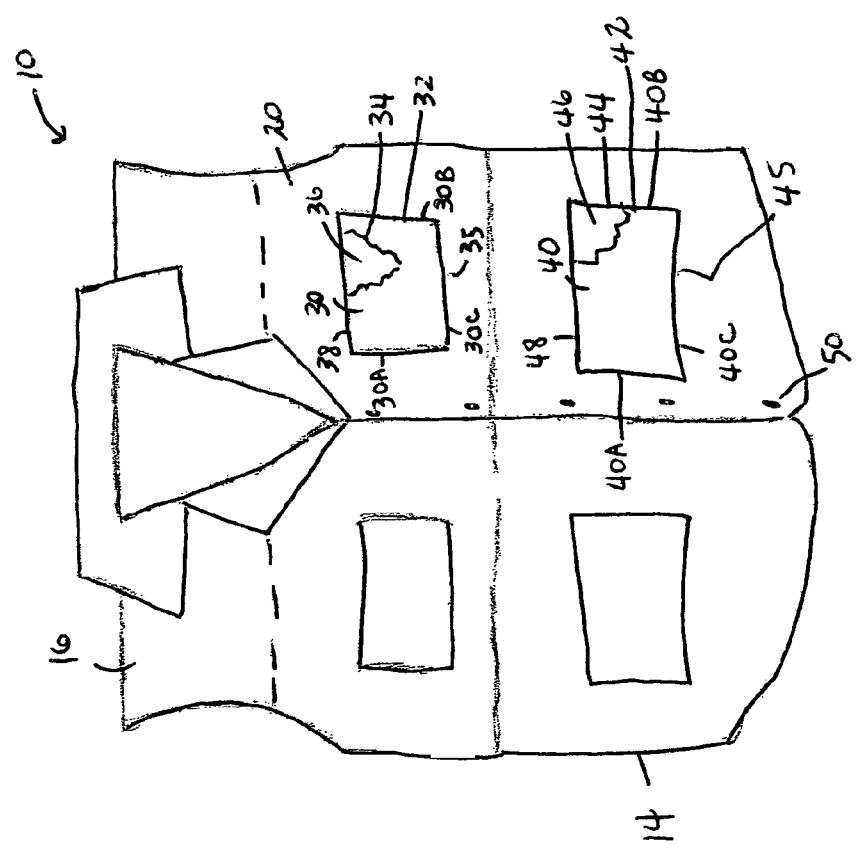

FIGS. 1-3 illustrate a preferred embodiment of a garment 10 made in accordance with the present invention. It should be noted that the garment 10 illustrated in the drawings is a sleeveless blouse design known in the art. It is understood that any article of clothing typically worn on the upper body such as a short sleeve shirt, long sleeve shirt, sweatshirt and the like is appropriate. The garment 10 includes a first vertical side 12 and a second vertical side 14. As is typical with articles of clothing, the garment 10 further includes an outer side 15 (shown in FIG. 1) that is usually of color or design in order to be aesthetically pleasing, and an inner side 16 (shown in FIG. 2) that is in contact with the wearer (not shown) when worn. As should be understood, both the outer and inner sides 15, 16 include the first and second vertical sides 12, 14 as disclosed.

The first vertical side 12 is disposed adjacent the second vertical side 14. For purposes of this disclosure, the first vertical side 12 includes components and is configured identical to the second vertical side 14. In the following description of the garment 10, only the configuration of the first vertical side 12 will be described in detail, while the identical configuration of the second vertical side 14 are also shown in the drawings. From the outside 15 of the garment 10, chambers 26 and 36 do not show are or are nearly invisible giving a more attractive garment.

Referring to FIG. 2, the inner side 16 includes a first layer 20, a seam 22 attaching the first layer 20 to the inner side 16, and preferably thermal material 24 (shown by cutaway) disposed between the first layer 20 and the inner side 16. The thermal material 24 can be insulating to hold in heat or cold and might also create a moisture barrier to prevent moisture that might condense on a cold pack from transferring through or creating a visible wet spot on the outside 15 of the garment 10. The first layer 20 is flat and having a generally rectangular configuration and having a width 25 of generally several inches such that the first layer 20 is disposed over a breast region of the wearer. The inner side 16 and first layer 20 define a chamber 26 for receiving hot or warm therapy such as a breast pack 100, 101. In this regard, an opening 28 is defined between the top of the first and second end seams 20A and 20B to access the chamber 26. The seam 20A can overlay the normal edge of the garment adjacent button fasteners 50 and the second seam 20B corresponds to a natural garment seam under the arm of the wearer. Thus in manufacture, the chamber 26 can be formed with a minimum of additional sewing only requiring the additional seam 22. Seams 20A, 20B and 22 fasten both layers 20 and 24 to the interior 16 of the garment 10.

A side opening 29 can be disposed along second end seam 20B. The side opening 29 is in communication with the chamber 26 and sized to release a drainage tube 55 for example, from the chamber 26. The drainage tube 55 can drain moisture from the chamber 26 if it is watertight or from a hot or cold pack 100, 101 contained within the chambers 26, 36, or the tube 55 might be a medical requirement for an I.V. or wound drain for example.

Seam 22 is formed by stitching or heat-sealing for example, and fastens the first layer 20 to the inner side 16 along ends 20A, 20B, and 20C. The sealed-together first layer 20 and inner side 16 define the chamber 26 for accommodating the female breast when a breast pack for example is in use.

Referring to FIG. 3, the inner side 16 can further include a second layer 30, a seam 32 attaching the second layer 30 to the first layer 20, and preferably thermal material 34 disposed between the first and second layers 20, 30 respectively. The second layer 30 is flat and can have a generally rectangular configuration and having a width 35 substantially less than the width 25 of the first layer 20 such that the second layer 30 is primarily disposed over the nipple area (not shown) of the wearer. The first layer 20 and second layer 30 define a second chamber 36 (shown by cutaway in FIG. 3) for receiving hot or warm therapy 100, 101 such as a breast pack. In this regard, an a second opening 38 is defined between first and second end 30A and 30B to access the second chamber 36. Thus a second chamber 36 within a chamber 26 is created and access to the second chamber 36 is provided through the openings 28 and 38.

Seam 32 is formed by stitching or heat-sealing for example, and fastens the second layer 30 and a thermal layer 34 to the first layer 20 along ends 30A, 30B, and 30C. The sealed-together second layer 30 and first layer 20 define the chamber 36 for accommodating the female breasts when a breast pack for example is in use.

The operation of the garment 10 for therapeutic comfort to women experiencing breast discomfort will now be described. The wearer places the garment 10 on her body with arms through openings 60 similar to any other article of clothing such as a vest typically worn on the upper body. When worn, the chambers 26 of the first vertical side 12 and second vertical side 14 are positioned and in contact with the breasts. If cold compression is desired, cooling packs 100, 101 are inserted in the chambers 26 through the openings 28. As a consequence, the cooling packs are positioned between the breasts and the second and first layers 30, 20 respectively. In this regard, the cooling members are positioned on each breast from a position approximately adjacent an arm of the wearer towards a position at the center of the chest of the wearer thereby covering each breast. The packs 100, 101 can be small enough to be positioned within the chambers 26, 36 or can take up most of the chambers 26, 36 such that the pack is not free to move. The pack 101 in the large chamber 26 could use an attachment means such as a loop pile fastener or adhesive to hold it in a specific position. Similarly, if warm compression is desired, warming members are inserted into the chambers 26 and positioned between the breasts and the second and first layers 30, 20 respectively.

If cold or warm therapy is desired specifically over the nipple area, application of the garment 10 is similar as described above except that the selected cold or warm packs are inserted into the chambers 36. Thereafter, the cold or warm members are positioned between the breasts and the second layer 30, directly over the nipple area.

Referring to FIG. 3, the inner side 16 can further include a lower layer 40, a seam 42 attaching the lower layer 40 to the inner side 16, and preferably thermal material 44 disposed between the lower layer 40 and the inner side 16. The lower layer 40 is flat and having a generally rectangular configuration and having a width 45 substantially similar to the width 25 of the first layer 20. As illustrated, the lower layer 40 is disposed below the seam 22 near or adjacent the wearer's abdominal area.

The lower layer 40 and inner side 16 define a chamber 46 for receiving hot or warm therapy (not shown). In this regard, an opening 48 is defined between first and second ends 40A and 40B to access the chamber 46.

Seam 42 is formed by stitching or heat-sealed for example, and fastens the lower layer 40 to the inner side 16 along ends 40A, 40B, and 40C. The sealed-together lower layer 40 and inner side 16 define the chamber 46 for accommodating the wearer's abdominal area when hot or warm therapy to the abdominal area is desired. When the garment 10 is worn, the chamber 46 is positioned and in contact with the wearer's abdominal area. If cold compression is desired, cooling packs are inserted in the chamber 46 through the opening 48. As a consequence, the cooling pack is positioned between the abdominal area and the lower layer 40 and inner side 16. Similarly, if warm compression is desired, warming members are inserted into the chamber 46 and positioned between the abdominal area and the lower layer 40 and inner side 16.

While the preferred embodiments of the invention have been shown, illustrated, and described, it would be apparent to those skilled in this field that various modifications may be made in these embodiments without departing from the spirit of the present invention.

Thus the scope of the invention should be determined by the appended claims in the formal application and their legal equivalents, rather than by the examples given.

I claim:

1. A garment for therapeutic comfort to women experiencing breast discomfort, said garment comprising:
   an inner side, said inner side comprising a first vertical side, a second vertical side, wherein said first vertical side is adjacent said second vertical side,
   first layers attached to said first vertical side and said second vertical side such that each first layer is disposed over a breast region of the wearer,
   first chambers defined between each said first layer and the inner side, each said first chamber for receiving hot or warm therapy,
   first openings at a top of said first chambers to provide access to said first chambers, wherein said garment further including second layers attached to each said first layers such that each said second layer is adapted to be disposed over a nipple area of the wearer,
   second chambers defined between each said first and second layers, each said second chamber for receiving hot or warm therapy,
   second openings defined between first and second ends of each said second layers to access each said second chambers.

2. The garment as recited in claim 1, wherein said garment further includes lower layers attached to the first vertical side and the second vertical side such that each said lower layer is adapted to be disposed over an abdominal region of the wearer,
  lower chambers defined between each said lower layer and the inner side, each said lower chambers for receiving hot or warm therapy,
  lower openings defined between first and second ends of each said lower layer, each said lower opening to access each said chambers.

3. The garment as recited in claim 1, including a side opening in said first chambers, said side opening receiving a drainage tube to drain moisture from said first chambers.

4. The garment as recited in claim 1, wherein a thermal material layer is disposed between said first layer and said inner side to hold heat from transferring between said first layer through to said inner side.

5. The garment as recited in claim 1, wherein a moisture barrier is disposed between said first layer and said inner side to prevent transfer of moisture from said hot or warm therapy to said inner side.

6. A garment for therapeutic comfort to women experiencing breast discomfort, said garment comprising:
  an inner garment side,
  a first layer of material attached to said inner garment side such that said first layer of material is adapted to be disposed over a breast region of the wearer,
  a first chamber defined between said first layer of material and the inner side, said first chamber for receiving first thermal therapy,
  a first opening at a top edge of said chamber, said first opening providing access to said chamber,
  a second chamber smaller than said first chamber, said second chamber formed within said first chamber.

7. The garment as recited in claim 6, including a thermal and moisture barrier formed between said first layer and said inner garment side.

8. The garment as recited in claim 7, including a side opening in said first chamber, said side opening receiving a drainage tube to drain moisture from said first chamber.

9. The garment as recited in claim 8, wherein said second chamber is disposed on said first layer such that when said garment is worn said second chamber is located over a breast nipple area of the wearer.

10. The garment as recited in claim 9, wherein said garment includes a third chamber below said first chamber such that said third chamber is adapted to be adjacent the abdomen of said wearer.

11. A garment for therapeutic comfort to women experiencing breast discomfort, said garment comprising:
  a first side and a second side of said garment each side including an inner garment side,
  a first layer of material attached to said inner garment side such that said first layer of material is adapted to be disposed over a breast region of the wearer,
  a first chamber defined between said first layer of material and the inner side, said first chamber containing a first thermal pack having a first temperature,
  a first opening at a top edge of said chamber, said first opening providing access to said first chamber,
  a second chamber within said first chamber, said second chamber including a top opening providing access to said second chamber.

12. The garment as recited in claim 11, including a thermal and moisture barrier formed between said first layer and said inner garment side.

13. The garment as recited in claim 12, wherein said second chamber is disposed on said first layer such that when said garment is worn said second chamber is adapted to be located over a breast nipple area of the wearer, and said second chamber contains a second thermal pack having a second temperature.

14. The garment as recited in claim 12, wherein each side of said garment includes a third chamber below said first chamber such that said third chamber is adapted to be adjacent the abdomen of said wearer and wherein said third chamber contains a third thermal pack having a third temperature.

15. The garment as recited in claim 14, including a side opening in said first chamber, said side opening receiving a drainage tube to drain moisture from said first chamber.

* * * * *